(12) United States Patent
Jimenez-Bayardo et al.

(10) Patent No.: US 8,293,789 B2
(45) Date of Patent: Oct. 23, 2012

(54) METHOD OF PREPARING A LATANOPROST OPTHALMIC SOLUTION AND THE RESULTING SOLUTION

(76) Inventors: Arturo Jimenez-Bayardo, Guadalajara (MX); Jose Ruben Tornero-Montaño, Guadalajara (MX); Maria Isabel Lopez-Sanchez, Guadalajara (MX); Enrique Cruz-Olmos, Guadalajara (MX)

( * ) Notice: Subject to any disclaimer, the term of this patent is extended or adjusted under 35 U.S.C. 154(b) by 1238 days.

(21) Appl. No.: 11/597,459

(22) PCT Filed: May 26, 2004

(86) PCT No.: PCT/MX2004/000034
§ 371 (c)(1),
(2), (4) Date: Sep. 21, 2007

(87) PCT Pub. No.: WO2005/115401
PCT Pub. Date: Dec. 8, 2005

(65) Prior Publication Data
US 2008/0021101 A1    Jan. 24, 2008

(51) Int. Cl.
*A61K 31/19* (2006.01)
*A61K 31/215* (2006.01)
(52) U.S. Cl. ........................ 514/530; 514/573
(58) Field of Classification Search .................. 514/530, 514/573
See application file for complete search history.

(56) References Cited

U.S. PATENT DOCUMENTS
2001/0046982 A1   11/2001   Maxey et al.
2002/0103255 A1   8/2002   Hellberg et al.

FOREIGN PATENT DOCUMENTS
EP      0 603 800 A1   6/1994
EP      1 142 576 A1   10/2001
WO     WO 97/29752    8/1997
WO     WO 02/38158 A1   5/2002

OTHER PUBLICATIONS

Xalatan Latanoprost Opthalmic Drug Information . . . , http://www.rxlist.com/xalatan-drug.htm (1 page), 2012.
The Merck Index (14th Edition), 2006, pp. 932 and 933.
Physicians Desk Reference 2003, p. 2793.

*Primary Examiner* — Zohreh Fay
(74) *Attorney, Agent, or Firm* — Husch Blackwell LLP

(57) ABSTRACT

A method of solubilizing an analog active agent of the prostaglandin F2α, such as latanoprost, is described and a method of preparing an ophthalmic solution of the solubilized latanoprost for the treatment of distinct ocular ailments. This invention also refers to an ophthalmic aqueous solution resulting from the aforementioned method, which is characterized by its chemical stability at room temperature, its safety, and innocuousness and efficiency in the treatment of the patient. The new ophthalmic aqueous solution is distinguished because its pharmaceutical value is found in the handling of a vehicle of easy access that not only permits the solubility of latanoprost, but also promotes its chemical stability and a greater tolerance of the patient with its ophthalmic application for the treatment of the patient's ailment.

4 Claims, 1 Drawing Sheet

METHOD OF PREPARING A LATANOPROST OPTHALMIC SOLUTION AND THE RESULTING SOLUTION

RELATED APPLICATIONS

This application is the U.S. National Phase filing under 35 U.S.C. §371 of PCT/MX2004/000034, filed May 26, 2004, which designated the United States and was published in a language other than English. The content of this application is incorporated herein by reference in its entirety.

BACKGROUND OF THE INVENTION

1. Field of the Invention

The invention relates to a latanoprost ophthalmic solution and a method of preparing same, which is chemically stable at room temperature, and which offers greater efficiency, safety and performance in the treatment of distinct ailments of the eye.

2. Description of Prior Art

The analogs of the prostaglandins are some of the most recent additions to the list of hypotensive ocular medicines available for the treatment of glaucoma. The main mechanism of action of these agents for the reduction of intraocular pressure is, as has been observed in the performed studies, by means of the increase of the elimination of the aqueous humor by means of the conventional path or uveosderal path. This mechanism consists of the action of these compounds on specific prostanoid receptors of the ciliary muscles and, furthermore, it favors the biosynthesis of metalloproteins of the uterus, a family of proteins that can attach themselves to the components of the extracellular uterus. The above alters the content of collagen in the ciliary muscle, whereby there is a reduction in the hydraulic resistance of the uveoscleral path.

Latanoprost is an analog of the prostaglandin F2α which is used to treat the open angle glaucoma; it is a selective agonist of the FP prostanoid receptor which reduces the intraocular pressure, increasing the outflow of the aqueous humor. Studies on animals and humans indicate that the main mechanism of action is an increased uveoscleral outflow.

Latanoprost is a colorless or slightly yellow oily liquid, highly soluble in acetonitrile and freely soluble in acetone, ethanol, ethyl acetate, isopropanol, methanol and octanol. It is practically insoluble in water. Latanoprost is the isopropilic ester of the prostaglandin F2α 17-phenyl-13,14dihydro (17-phenyl-13,14dihydro PGF2α). It is presented in the form of prodrug of free acid, which is a potent agonist of the FP receptors of the eye. Latanoprost reduces intraocular pressure in patients with glaucoma.

Latanoprost is a prodrug that is well absorbed via the cornea, being activated by hydrolysis to the active form of latanoprost acid. The peak concentration in the aqueous humor is reached 2 hours after local administration. The latanoprost acid is practically not metabolized in the eye. Its principal metabolism occurs in the liver giving inactive metabolites that are mostly excreted in the urine. The plasmatic mid life in humans is of 17 minutes.

The formula of latanoprost is $C_{26}H_{40}O_5$ and it has a molecular weight of 432.85, it is an isopropilic ester prodrug, which alone is inactive, but following hydrolysis it becomes biologically active. The prodrug is fully absorbed via the cornea and all the drug that enters the aqueous humor is hydrolyzed during the passage through the cornea.

Studies on humans indicate that the maximum concentration in the aqueous humor is reached approximately two hours following its administration.

It has been demonstrated that one sole daily application of latanoprost (0.005%) is most effective, or at least as effective as a double daily application of other agents utilized in glaucoma therapy, in the reduction of the intraocular pressure in patients with open angle glaucoma or ocular hypertension. Most patients treated with latanoprost reached a neutral level of intraocular pressure after 6 months of treatment in relation to patients treated with other hypotensive agents, observing a reduction in the intraocular pressure of at least 30% in 52% of the patients treated with latanoprost.

Another benefit of latanoprost seems to be a more uniform circadian reduction of intraocular pressure, while timolol is less effective during the night. Dorzolamide is less effective than latanoprost but permits a significant reduction in nocturnal intraocular pressure.

There are studies in which latanoprost has shown additive effects ranging from 13% to 37% when combined with timolol which exceed the effects shown by joint therapies using combinations of timolol with pilocarpine, brimonidine and dorzolamide. There also exists a precedent of unoprostone combined with β-blockers where significant hypotensive effects were found.

Studies have been performed by distinct investigators in order to compare the effectiveness of latanoprost with respect to unoprostone as hypotensive agents, observing better results in patients treated with latanoprost, presenting similar side effects.

Medicines applied to the surface of the eye should meet certain characteristics of pH, osmolarity, conductivity, continuance time and clarity of vision following application, in order to be accepted by patients. However, in the case of latanoprost, and other therapeutic active ingredients insoluble in water, are generally prepared in solutions that present numerous inconveniences, with the most important one being the accelerated degeneration of the active ingredient at room temperature.

SUMMARY OF THE INVENTION

One important object of the invention is to propose a method of solubilizing latanoprost in order to prepare a new ophthalmic aqueous solution, chemically stable at room temperature, which resolves the inconveniences of the currently available solutions of latanoprost.

Another object of this invention is to provide a method of preparing a new ophthalmic aqueous solution of latanoprost for the treatment of distinct eye ailments.

Another principal object of the invention is to provide a new ophthalmic aqueous solution of latanoprost, which resolves the inconveniences of the currently available latanoprost solutions, whose degradation is presented in less time. To this end, a new ophthalmic solution is proposed, whose formula includes ingredients not contained in other latanoprost ophthalmic solutions, such as cydodextrins, which due to their own characteristics and in combination with other elements of the formula produce a latanoprost ophthalmic solution, chemically stable at room temperature.

The cyclodextrins are neutral and natural macrocyclic oligosaccharides, containing various units of (+)-glucopyranose. The cyclodextrins are obtained by an enzymatic treatment of the starch. Its shape is similar to a truncated cone with a cavity of variable dimensions (depth and width) depending on the number of units of glucopyranose.

The formation of complexes of inclusion with cyclodextrins is a technological resource that has permitted the improvement of certain physicochemical properties of the complex molecules such as their solubility and stability. The principal mechanism of the cyclodextrins, which includes the formation of complexes by inclusion of analytes, is based on a dynamic balance in which water or another compound is replaced with another host in the cavity of the cyclodextrin molecule.

The inclusion of hydroxypropylbetacyclodextrins together with sodium hyaluronate in a new ophthalmic solution of this invention provides a protective and beneficial environment for the latanoprost molecule, because the active ingredient is housed in the lipophilic cavity of the cyclodextrins and at the same time the hydrophilic surface contributes to the solubility in water, while the sodium hyaluronate covers the formed complex. The interaction of the drug with the hydroxypropylbetacyclodextrins and the sodium hyaluronate results in the reduction of the decomposition, which grants protection to the active labile in an aqueous environment.

In a preferred embodiment of the invention, the aqueous ophthalmic solution is characterized by including latanoprost at a concentration of 0.005%; a pH damper system that may be selected from boric acid, citric acid, sorbic acid, acetic acid, sodium borate, monobasic sodium phosphate, dibasic sodium phosphate, sodium citrate and sodium acetate, in a range of concentration from 0.001% to 5.0%; one or more agents that increase the viscosity, such as hydroxypropylcellulose, carbooxylmethylcellulose, sulfate chondrointin, formal glycerol, methyidinoglycerol and cyclodextrins, in a concentration ranging from 0.05% to 20.00%; one or more tensoactive agents, moisturizers such as polyoxyl 40 stearate, polysorbate 80, poloxamer and tyloxapol, in concentrations ranging from 0.01% to 20.0%; one or more osmolarity regulating agents such as sodium chloride, sorbitol, manitol and dextrose at a concentration ranging from 0.6% to 1.8%, expressed as chemical equivalents of sodium chloride; one or more preservatives such as benzalkonium chloride, benzetonium chloride, thiomersal, phenylmercury acetate or nitrate, parabens, chlorohexidine gluconate, ethylic alcohol, cetrimide, sodium perborate and chlorobutanol in adequate concentration in order to provide an antimicrobian effect. It may also contain one or more antioxidant agents such as disodic edetate, sodium metabisulfite, sodium bisulfite, acetylcysteine, sodium thiosulfate and thiourea in adequate concentration in order to give the required effect.

The preferred concentrations of the preservatives are, for example: 0.005% to 0.02% of benzalkonium chloride, a maximum of 0.01% of benzetonium chloride, 0.005% to 0.02% of thiomersal, 0.002% to 0.004% of phenylmercury acetate or nitrate, a maximum of 0.002% of parabens, 0.002% to 0.01% of chlorohexidine gluconate and 0.15% to 0.5% of chlorobutanol.

All the above proposed methodology and formulation provide a new ophthalmic aqueous solution of latanoprost which upon preserving for a longer time the highest availability of this prodrug in the solution, shall necessarily yield the best results in the treatment of the patient's ailment.

DETAILED DESCRIPTION OF THE PREFERRED EMBODIMENTS OF THE INVENTION

Figure 1:
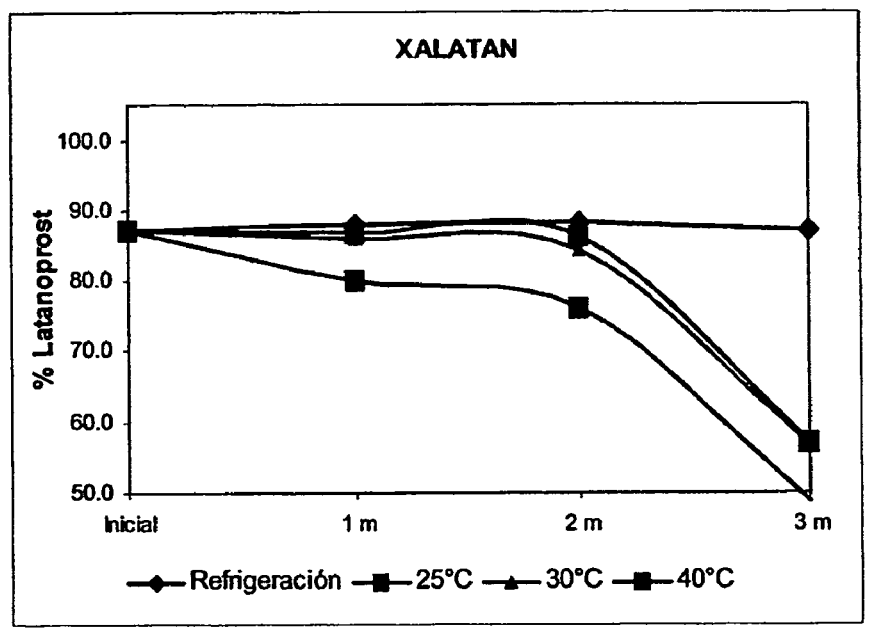
FIG. 1 is representative graph of the behavior of latanoprost in a conventional ophthalmic solution that has been submitted to stability studies at distinct storage temperatures.

This invention refers to a method of solubilization of latanoprost, a method of preparing an ophthalmic aqueous solution of latanoprost and said resulting solution whose clinical value is seen to be reflected in the safety, stability of the active ingredient, innocuousness and treatment of the patient. The pharmaceutical value of the new ophthalmic solution is found in the handling of a vehicle of easy access, which not only permits the solubility of latanoprost, but also favors the stability of the product at room temperature with a greater tolerance on the part of the patient.

Hereupon, some examples of the method and of the resulting ophthalmic solution are described in preferred embodiment thereof; however, such examples should by no means be interpreted in a limitative sense, but rather as possible realization methods that may eventually be modified without thus being separated from the concept of this invention.

Formulation of Latanoprost at 0.005% (100 L)

Phase 1. Preparation of a Vehicle Solution. (Solution A)
1. In a stainless steel tank, 70 liters of purified water are poured at 30°±2° C.
2. Agitation is commenced at between 500 and 550 rpm and is maintained constant during the entire preparation process.
3. 7.5 kg of hydroxypropylbetacyclodextrins are added, while maintaining the agitation for approximately 10 minutes to allow that it dissolves.
4. 700 g of monobasic phosphate of monohydrated sodium is added and it is left for 5 minutes until fully dissolved.
5. 600 g of dibasic phosphate is added and it is left for 5 minutes until fully dissolved.
6. 30 L of this solution are separated for solution B and for the subsequent rinses and the rest is added to the following raw materials:
7. 200 g of sodium hyaluronate are added slowly while maintaining the agitation for 25 to 35 minutes.
8. 44 g of benzalkonium chloride (solution at 50%) are added, which have previously been dissolved in purified water, and left for 5 minutes until it is fully integrated.
9. Keep 30 L for subsequent rinses.

Phase 2. Solubilization of Latanoprost. (Solution B)
1. 5.000 g of latanoprost are placed into a 50 L recipient.
2. 15 L of solution A are added in order to dissolve by means of constant agitation.
3. The recipient containing latanoprost is rinsed thoroughly and the wash is added to solution C.

Phase 3. Preparation of an Aqueous Ophthalmic Solution of Latanoprost. (Solution C)
1. Add solution B to solution A while the latter continues to be agitated at 500 to 550 rpm.
2. Repeatedly rinse the recipient of solution B with the remaining 15 L of solution A, adding the rinses of solution C.
3. Top up the volume to 100 L with purified water and continue to agitate at 500 to 550 rpm for approximately one hour more in order to homogenize.

The novelty aspect of the previously described method in found in the composition of the formula, the order in which the compounds are added and the temperature of the solution during each step of the process. The result is classified as being novel given that there exists no description in which an ophthalmic aqueous solution of latanoprost is prepared that is stable at room temperature, which possesses the characteristics of the solution resulting from the previously described method.

In a preferred embodiment of the invention, the ophthalmic aqueous solution, obtained by means of the previously described method, is characterized in that it includes: latanoprost at a concentration of 0.005%; a pH damper system that may be boric acid, citric acid, sorbic acid, acetic acid, sodium borate, monobasic sodium phosphate, dibasic sodium phosphate, sodium citrate and sodium acetate, in a range of concentration from 0.001% to 5.0%; one or more agents that increase the viscosity such as hydroxypropylcellulose, carbooxylmethylcellulose, methylcellulose, polyvinylic alcohol, sodium hyaluronate, sulfate chondrointin, glycerin, formal glycerol, methyldinoglycerol and cyclodextrins, in concentrations ranging from 0.05% to 20.00%; one or more tensoactive agents, moisturizers such as polyoxyl 40 stearate, polysorbate 80, poloxamer and tyloxapol, in concentrations ranging from 0.01% to 20.0%; one or more osmolarity regulating agents such as sodium chloride, sorbitol, manitol and dextrose, at a concentration ranging from 0.6% to 1.8%, expressed as chemical equivalents of sodium chloride; one or more preservatives such as benzalkonium chloride, benzetonium chloride, thiomersal, phenylmercury acetate or nitrate, parabens, chlorohexidine gluconate, ethylic alcohol, cetrimide, sodium perborate and chlorobutanol in adequate concentration in order to provide a antimicrobian effect. It may also contain one or more antioxidant agents such as disodic edetate, sodium metabisulfite, sodium bisulfite, acetylcysteine, sodium thiosulfate and thiourea in adequate concentration in order to give the required effect.

The preferred concentrations of the preservatives are, for example: 0.005% to 0.02% of benzalkonium chloride, a maximum of 0.01% of benzetonium chloride, 0.005% to 0.02% of thiomersal, 0.002% to 0.004% of phenylmercury acetate or nitrate, a maximum of 0.002% of parabens, 0.002% to 0.01% of chlorohexidine gluconate and 0.15% to 0.5% of chlorobutanol.

Stability Studies of the New Ophthalmic Solution

In order to verify the stability of the new ophthalmic solution of latanoprost, stability studies were performed, using for such purpose, three different product lots, for which purpose the following product storage conditions and sampling times were taken into account:
Refrigeration (2° C.-8° C.): 3, 6 and 9 months.
Room Temperature (15° C.-30° C.): 1, 3, 4, 5, 6 and 9 months.
30° C. and 40° C.: 1, 2, 3, 4, 5 and 6 months.

Analysis of Data and Results

Determinations were undertaken of: Appearance, pH, Osmolarity and Assessment of Latanoprost, using the pharmacopoeia of the Mexican United States and the United States of America pharmacopoeia as a reference.

| LOT JL3045 | | | | | |
|---|---|---|---|---|---|
| Determination | | Appearance | pH 6.2-7.2 | Osmolarity 250-350 | Latanoprost 90.0%-110.0% |
| Temperature | Months | TCVSFVP* | | mOsm/Kg | |
| Refrigeration (2° C.-8° C.) | 0 | TCVSFVP | 6.73 | 300 | 101.4 |
| | 3 | TCVSFVP | 6.72 | 297 | 94.9 |
| | 6 | TCVSFVP | 6.70 | 297 | 99.9 |
| | 9 | TCVSFVP | 6.69 | 291 | 102.0 |
| Room Temperature (15° C.-30° C.) | 1 | TCVSFVP | 6.76 | 296 | 99.1 |
| | 3 | TCVSFVP | 6.73 | 293 | 95.2 |
| | 4.5 | TCVSFVP | 6.73 | 307 | 105.1 |
| | 6 | TCVSFVP | 6.70 | 303 | 103.4 |
| | 9 | TCVSFVP | 6.70 | 288 | 106.2 |
| 30° C. | 1 | TCVSFVP | 6.76 | 296 | 99.6 |
| | 2 | TCVSFVP | 6.63 | 295 | 100.8 |
| | 3 | TCVSFVP | 6.73 | 306 | 96.4 |
| | 4.5 | TCVSFVP | 6.73 | 303 | 104.1 |
| | 6 | TCVSFVP | 6.70 | 311 | 100.6 |
| 40° C. | 1 | TCVSFVP | 6.81 | 296 | 99.8 |
| | 2 | TCVSFVP | 6.62 | 302 | 100.9 |
| | 3 | TCVSFVP | 6.72 | 305 | 97.0 |
| | 4.5 | TCVSFVP | 6.69 | 355 | 105.2 |
| | 6 | TCVSFVP | 6.68 | 349 | 106.8 |

*TCVSFVP = Transparent colorless, viscose solution and free of Visible particles

| LOT JL3055 | | | | | |
|---|---|---|---|---|---|
| Determination | | Appearance | pH 6.2-7.2 | Osmolarity 250-350 | Latanoprost 90.0%-110.0% |
| Temperature | Months | TCVSFVP* | | mOsm/Kg | |
| Refrigeration (2° C.-8° C.) | 0 | TCVSFVP | 6.73 | 300 | 101.3 |
| | 3 | TCVSFVP | 6.76 | 296 | 96.7 |
| | 6 | TCVSFVP | 6.72 | 296 | 108.5 |
| | 9 | TCVSFVP | 6.70 | 293 | 95.5 |
| Room Temperature (15° C.-30° C.) | 1 | TCVSFVP | 6.80 | 298 | 98.1 |
| | 3 | TCVSFVP | 6.75 | 301 | 96.7 |
| | 4.5 | TCVSFVP | 6.72 | 295 | 103.3 |
| | 6 | TCVSFVP | 6.72 | 300 | 102.3 |
| | 9 | TCVSFVP | 6.70 | 295 | 99.8 |
| 30° C. | 1 | TCVSFVP | 6.81 | 298 | 98.6 |
| | 2 | TCVSFVP | 6.64 | 295 | 101.6 |
| | 3 | TCVSFVP | 6.75 | 312 | 99.1 |
| | 4.5 | TCVSFVP | 6.73 | 301 | 104.5 |
| | 6 | TCVSFVP | 6.72 | 306 | 101.6 |
| 40° C. | 1 | TCVSFVP | 6.80 | 296 | 102.7 |
| | 2 | TCVSFVP | 6.63 | 300 | 101.6 |
| | 3 | TCVSFVP | 6.74 | 309 | 98.5 |
| | 4.5 | TCVSFVP | 6.69 | 320 | 105.6 |
| | 6 | TCVSFVP | 6.70 | 350 | 102.4 |

*TCVSFVP = Transparent colorless, viscose solution and free of Visible particles

| LOT JL3065 | | | | | |
|---|---|---|---|---|---|
| Determination | | Appearance | pH 6.2-7.2 | Osmolarity 250-350 | Latanoprost 90.0%-110.0% |
| Temperature | Months | TCVSFVP* | | mOsm/Kg | |
| Refrigeration (2° C.-8° C.) | 0 | TCVSFVP | 6.73 | 300 | 103.0 |
| | 3 | TCVSFVP | 6.76 | 298 | 97.4 |
| | 6 | TCVSFVP | 6.72 | 313 | 110.2 |
| | 9 | TCVSFVP | 6.70 | 283 | 96.1 |
| Room Temperature (15° C.-30° C.) | 1 | TCVSFVP | 6.80 | 290 | 99.9 |
| | 3 | TCVSFVP | 6.75 | 298 | 101.0 |
| | 4.5 | TCVSFVP | 6.72 | 302 | 105.9 |
| | 6 | TCVSFVP | 6.72 | 300 | 100.7 |
| | 9 | TCVSFVP | 6.70 | 291 | 109.3 |
| 30° C. | 1 | TCVSFVP | 6.81 | 292 | 100.0 |
| | 2 | TCVSFVP | 6.64 | 297 | 102.2 |
| | 3 | TCVSFVP | 6.75 | 303 | 103.7 |
| | 4.5 | TCVSFVP | 6.73 | 308 | 104.9 |
| | 6 | TCVSFVP | 6.72 | 322 | 104.8 |
| 40° C. | 1 | TCVSFVP | 6.80 | 296 | 101.3 |
| | 2 | TCVSFVP | 6.63 | 306 | 108.1 |
| | 3 | TCVSFVP | 6.74 | 317 | 106.4 |
| | 4.5 | TCVSFVP | 6.69 | 321 | 108.5 |
| | 6 | TCVSFVP | 6.70 | 327 | 102.5 |

*TCVSFVP = Transparent, colorless, viscose solution and free of Visible particles In the stability study, no significant changes in the analyzed parameters. The ophthalmic solution maintains all of its determinations within the specifications.

Furthermore, a comparative stability study was performed of the new ophthalmic solution and another one available on the market. The results of said study are specified hereunder.

I. STABILITY STUDY OF LATANOPROST IN DIFFERENT OPHTHALMIC SOLUTIONS

A stability study of an ophthalmic solution of latanoprost was performed in order to verify the behavior of the product identified by the trademark XALATAN®, by submitting this one to stability and comparing it to the new formulation of this invention.

The label of the XALATAN® product specifies that the product should be protected from light and, prior to opening, it should be stored between 2° C. and 8° C. During shipping, the product may remain at a temperature of up to 40° C. for a maximum of 8 days. Once the bottle is opened for use, it should be stored at a temperature of no more than 25° C. for 6 months.

For purposes of the comparative study between XALATAN® and the new aqueous solution, samples of the XALATAN® (Lot HB0990) product and samples of the new solution (F-7) were submitted to a stability study, in order to discover their degradation profile. The stability study was performed on samples at different temperatures: in Refrigeration (2° C.-8° C.), at 25° C., at 30° C. and at 40° C. Initially, on each date of analysis, the studies of Appearance determination, pH, assessment of latanoprost were performed by means of Chromatography of Liquids (HPLC).

II. RESULTS

The determinations of appearance and pH did not present significant variations at the different times and temperatures in any of the products. However, according to the performed studies, the content of latanoprost in XALATAN® was seen to be affected by the temperature, as shown in the values of Table 1:

TABLE 1

| XALATAN % Latanoprost (Labeled 0.005 g/100 ml) | | | | |
|---|---|---|---|---|
| Time | Refrigeration (2° C.-8° C.) | 25° C. | 30° C. | 40° C. |
| 0 | 87.2 | 87.2 | 87.2 | 87.2 |
| 1 month | 88.0 | 86.9 | 86.0 | 80.0 |
| 2 months | 88.4 | 86.4 | 84.4 | 76.2 |
| 3 months | 87.9 | 57.2 | 56.8 | 49.0 |

On the contrary, the content of latanoprost in the aforementioned formula claimed in this application, shows a more uniform behavior, as observed in the data of the following table 2:

TABLE 2

| New Solution % Latanoprost (Labeled 0.005 g/100 ml) | | | | |
|---|---|---|---|---|
| Time | Refrigeration (2° C.-8° C.) | 25° C. | 30° C. | 40° C. |
| 0 | 100.0 | 100.0 | 100.0 | 100.0 |
| 1 month | 100.0 | 101.4 | 100.8 | 99.2 |
| 2 months | 99.0 | 100.0 | 100.2 | 99.8 |
| 3 months | 98.8 | 99.4 | 99.2 | 99.6 |

III. CONCLUSIONS

Based on the performed study, it is confirmed that the temperature affects the degradation of XALATAN® ophthalmic solution. Whereas, the product of the new ophthalmic formulation of latanoprost shows better behavior when submitted to different storage conditions, with refrigeration not being necessary in order to conserve the properties thereof.

Figure 2:
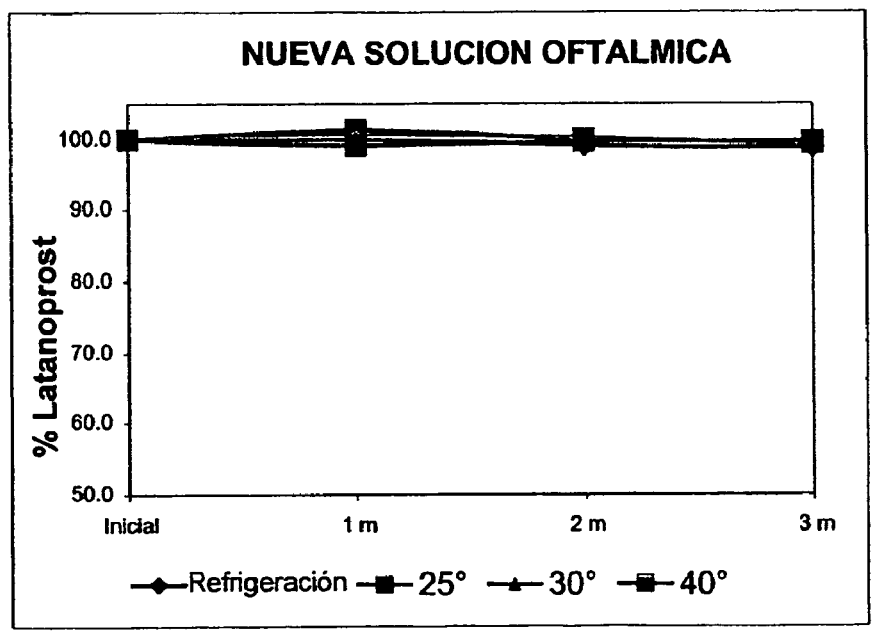
FIG. 2 is a representative graph of the behavior of a new ophthalmic aqueous solution of latanoprost that has been submitted to the same stability studies of the solution of the preceding figure.

FIGS. 1 and 2 represent in graphs, the behavior of both the ophthalmic solutions of latanoprost that were compared in said study.

Although the invention has been described in the preferred embodiments thereof, it shall be understood that specialists in the field would be able to make or propose changes, additions or modifications to the aforementioned methods and compositions that shall necessarily fall within the scope and spirit of the invention of the matter specified herein. Consequently, the interpretation of the novelty concepts of this invention should be in a broader sense in light of the content of the attached claims.

The invention claimed is:

1. Method of solubilizing latanoprost for preparing a chemically stable ophthalmic aqueous solution for the treatment of distinct ocular ailments, the method comprising:
    a) placing 5.000 g of latanoprost in a container;
    b) adding to the container, approximately 15 L of a solution containing 7.5% of hydroxypropylbetacyclodextrins, 0.7% of monobasic phosphate of monohydrated sodium, 0.6% of dibasic phosphate of anhydrous sodium and 0.2% of sodium hyaluronate, and agitate at 500 to 550 rpm in order to dissolve the latanoprost;
    c) waiting until it is fully dissolved and add to the solution, 0.005% to 0.02% of benzalkonium chloride, and always rinsing with the same solution with which the latanoprost was dissolved; and
    d) agitating until the solution is homogenized.

2. Method of preparing an ophthalmic aqueous solution of latanoprost, chemically stable at room temperature, for use in the treatment of ocular ailments; said method comprising the steps of:
    a) solubilizing a latanoprost;
    b) placing 5.0 g of latanoprost in a container and add 15 L of a solution containing 7.5% of hydroxypropylbetacyclodextrins, 0.7% of monobasic phosphate of monohydrated sodium, 0.6% of dibasic phosphate of anhydrous sodium and 0.2% of sodium hyaluronate, and agitate to 500 to 550 rpm in order to dissolve the latanoprost;
    c) waiting until the above solution is fully dissolved and adding 0.005% to 0.02% of benzalkonium chloride, agitating for 5 minutes until the solution is homogenized,
    d) preparing a vehicle solution; and
    e) mixing the solubilized latanoprost and the vehicle solution, and topping up the volume to 100 L with purified water, constantly agitating for a predetermined period.

3. The method of claim 1 or 2 in which the cyclodextrin is combined with the latanoprost in order to help it to dissolve and in order to protect it from hydrolysis.

4. Method of preparing an ophthalmic aqueous solution of latanoprost, chemically stable at room temperature, for use in the treatment of ocular ailments; said method comprising the steps of:
   a) solubilizing latanoprost;
   b) preparing a vehicle solution by
   c) pouring 70 liters of purified water in a stainless steel tank at 30°±2° C.;
   d) agitating the water between 500 and 550 rpm, which agitation is maintained constant during the entire preparation process;
   e) adding 7.5 kg of hydroxypropylbetacyclodextrins to the agitated water, while maintaining the agitation for approximately 10 minutes in order to dissolve;
   f) adding 700 g of monobasic phosphate of monohydrated sodium and leaving it for 5 minutes until fully dissolved;
   g) adding 600 g of dibasic phosphate of anhydrous sodium and it is left for 5 minutes until fully dissolved;
   h) separating 30 L of this solution for use in the solubilization of the latanoprost phase and for the subsequent rinses, and adding the rest to the following raw materials;
   i) adding 200 g of sodium hyaluronate slowly while maintaining the agitation for 25 to 35 minutes;
   j) adding 44 g of benzalkonium chloride (solution at 50%), which have previously been dissolved in purified water, and left for 5 minutes until it is fully integrated; and
   k) mixing the solubilized latanoprost and the vehicle solution, and top up the volume to 100 L with purified water, constantly agitating for a predetermined period.

\* \* \* \* \*